United States Patent
O'Mara et al.

(10) Patent No.: US 10,052,225 B2
(45) Date of Patent: Aug. 21, 2018

(54) DRUG-DISPENSING RING REMOVAL TOOL

(71) Applicants: Mary M. O'Mara, San Rafael, CA (US); Nathan Nick Moorhatch, Mill Valley, CA (US)

(72) Inventors: Mary M. O'Mara, San Rafael, CA (US); Nathan Nick Moorhatch, Mill Valley, CA (US)

( * ) Notice: Subject to any disclaimer, the term of this patent is extended or adjusted under 35 U.S.C. 154(b) by 0 days.

(21) Appl. No.: 14/999,725

(22) Filed: Jun. 20, 2016

(65) Prior Publication Data

US 2017/0367877 A1 Dec. 28, 2017
US 2018/0193184 A9 Jul. 12, 2018

Related U.S. Application Data

(60) Provisional application No. 62/217,042, filed on Sep. 11, 2015.

(51) Int. Cl.
*A61F 6/06* (2006.01)
*A61F 6/18* (2006.01)
*A61F 6/14* (2006.01)

(52) U.S. Cl.
CPC ............... *A61F 6/18* (2013.01); *A61F 6/142* (2013.01)

(58) Field of Classification Search
CPC .......................... A61F 16/18; A61F 16/142
See application file for complete search history.

(56) References Cited

U.S. PATENT DOCUMENTS

| | | | | |
|---|---|---|---|---|
| 3,077,879 | A * | 2/1963 | Knoch | A61F 6/142 128/839 |
| 3,410,269 | A * | 11/1968 | Novick | A61B 17/4208 606/125 |
| 3,635,215 | A * | 1/1972 | Shea | A61F 6/18 128/840 |
| 5,109,869 | A * | 5/1992 | Buckley | A61F 6/18 33/512 |
| 2007/0102003 | A1* | 5/2007 | Newman | A61F 6/12 128/837 |
| 2010/0300452 | A1* | 12/2010 | Tal | A61F 6/142 128/839 |
| 2016/0047074 | A1* | 2/2016 | Naka | D04B 3/02 66/118 |

FOREIGN PATENT DOCUMENTS

CN 202526376 U * 11/2012
WO WO-9938468 A1 * 8/1999 ............... A61F 6/12

* cited by examiner

*Primary Examiner* — Kristen Matter
(74) *Attorney, Agent, or Firm* — Law Office of Christopher Peil; Christopher Peil

(57) ABSTRACT

A drug dispensing ring removal tool with a rigid elongate member, a rigid hook member, a rigid flat plate member, a hook tip resilient member, a hook front end resilient member and a plurality of flat plate resilient members. The hook member is fixedly attached to the proximal end of the elongate member. The flat plate member fixedly attached to the distal end of the elongate member. The hook tip resilient member is fixedly attached to the end of the hook member. The hook front resilient member fixedly attached to the forward most end of the hook member. The flat plate resilient members fixedly attached within cutout portions of the flat plate member. The flat plate resilient members extend approximately one sixteenth of an inch above and below the planar surface of the flat plate member.

7 Claims, 4 Drawing Sheets

DRUG-DISPENSING RING REMOVAL TOOL

CROSS REFERENCE TO RELATED APPLICATIONS

Provisional patent application 62/217,042 filed on Sep. 11, 2015

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of removal tools for medically related products and more specifically to an estrogen ring removal tool.

In recent years, medications or other releasable chemicals have been imbedded into flexible rings which can be inserted into the vaginal canal of a woman so that the medication or chemical can be released and absorbed over time to the benefit of the user. One such ring is an estrogen ring which is prescribed by doctors for women who need to increase the available estrogen in the body. The ring is approximately two inches in diameter and can be squeezed into an ovoid shape for insertion into the vaginal canal. Although the insertion of the ring is relatively easy, the removal of the ring can be problematic. The user is asked to pull the ring out with her fingers, which can be difficult and uncomfortable. Some women make appointments with their gynecologists to have them remove it, which is time consuming and expensive. Other women try to use available hook type devices such as a crochet hook, to remove the ring, however this method can be quite dangerous because the hard edges of the hook can react negatively to the soft walls of the vaginal canal.

David Newman, in his patent application 20070102003 filed in 2005 discloses a tool for removing diaphragms, which are ring shaped, and used as a contraceptive device. The tool has a long handle with a dome shape at the end. The curved area between the underside of the dome and the handle is meant to engage the perimeter of the diaphragm and help pull it out of the vaginal passage.

However, there is a deficiency in this prior technology in that the dome shape is still made of hard material and the edges of the dome could cause discomfort to the user. Additionally, the design of the tool is more suited to a diaphragm which has a thin ring at its perimeter and a pliable sheet of material stretched over the ring which is in place over the cervix. It is not suitable for removal of a ring that has been squeezed to an ovoid shaped ring that is lodged in the vaginal canal, such as an estrogen ring.

BRIEF SUMMARY OF THE INVENTION

The primary object of the invention is to provide drug-dispensing ring removal tool that allows a woman to remove an estrogen ring or other similar ring from the vaginal canal in a safe and easy manner.

Another object of the invention is to provide drug-dispensing ring removal tool whose key touch points are made of soft resilient material.

Another object of the invention is to provide drug-dispensing ring removal tool that includes a stabilizing plate at the distal end of the tool to help the user hold the tool in a controlled manner.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed drug-dispensing ring removal tool comprising: a rigid elongate member, a rigid hook member, a rigid flat plate member, a hook tip resilient member, a hook front end resilient member, a plurality of flat plate resilient members, said hook member fixedly attached to the proximal end of said elongate member, said flat plate member fixedly attached to the distal end of said elongate member, said hook tip resilient member fixedly attached to the end of said hook member, said hook front resilient member fixedly attached to the forward most end of said hook member, said flat plate resilient members fixedly attached within cutout portions of said flat plate member, and said flat plate resilient members extending approximately one sixteenth of an inch above and below the planar surface of said flat plate member.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
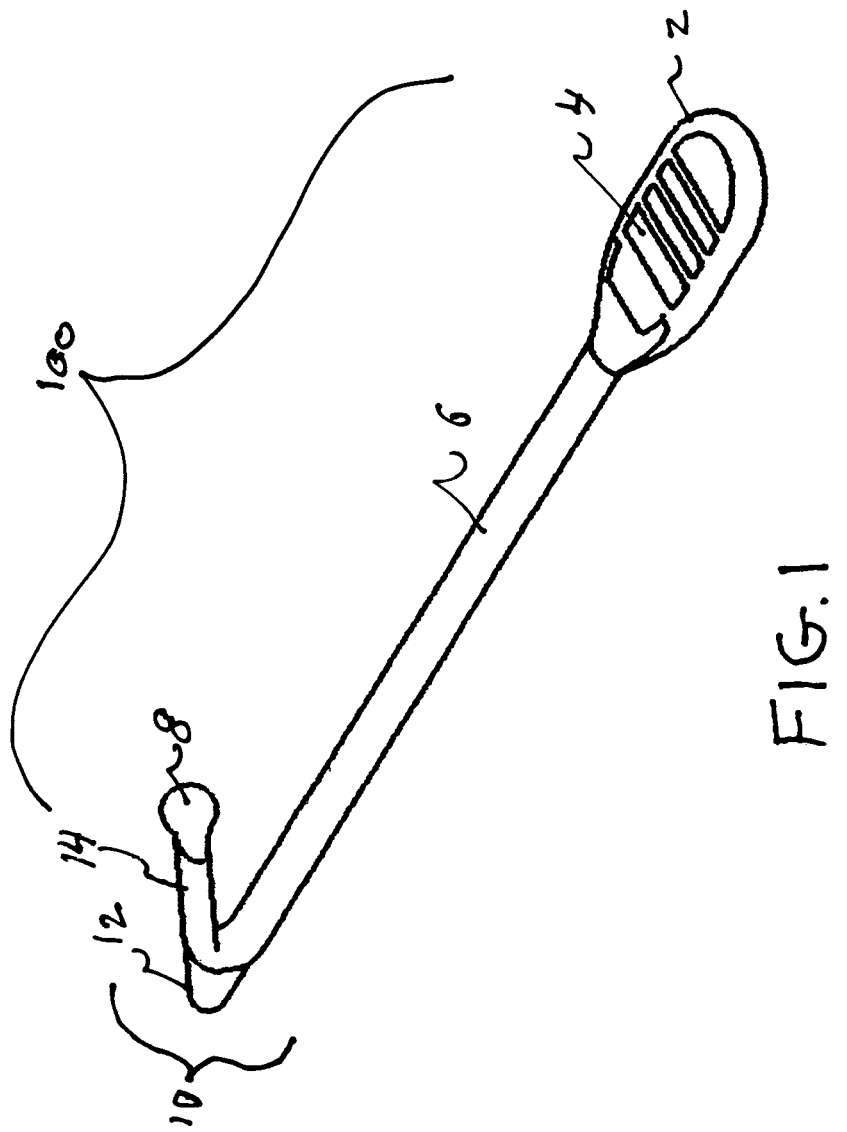
FIG. 1 is a perspective view of the invention.

Referring now to FIG. 1 we see a perspective view of the ring removal tool 100. A rigid elongate member 6 has a rigid hook member 14 fixedly attached to the proximal end, and a rigid flat plate member 2 fixedly attached to the distal end. The tip of the hook 10 includes a co-molded resilient member 12 which is made of a low durometer thermoplastic elastomer. A spherical shaped tip 8 is co-molded to the tip of the hook member 14. The tip 8 is also made of low durometer thermoplastic elastomer. The flat plate 2 includes cutouts that allow resilient plastic strips 4 to be co-molded in place. The strips 4 extend above and below the plate 2 by approximately seventy thousandths of an inch. These protruding strips 4 in combination with the flat plate 2 give the user more control of the ring removal tool 100 during use. During use, the user grasps the flat plate 2 with the fingers of one hand and inserts the tip 12 of the tool into the vaginal canal until it extends past the ring wall and then pulls the tool 100 out of the canal with the ring wall trapped in the V section of the hook 10. The soft and pliable nature of the tips 12 and 8 reduce the change of damage to the vaginal canal during use both during insertion and removal of the tool.

Figure 2:
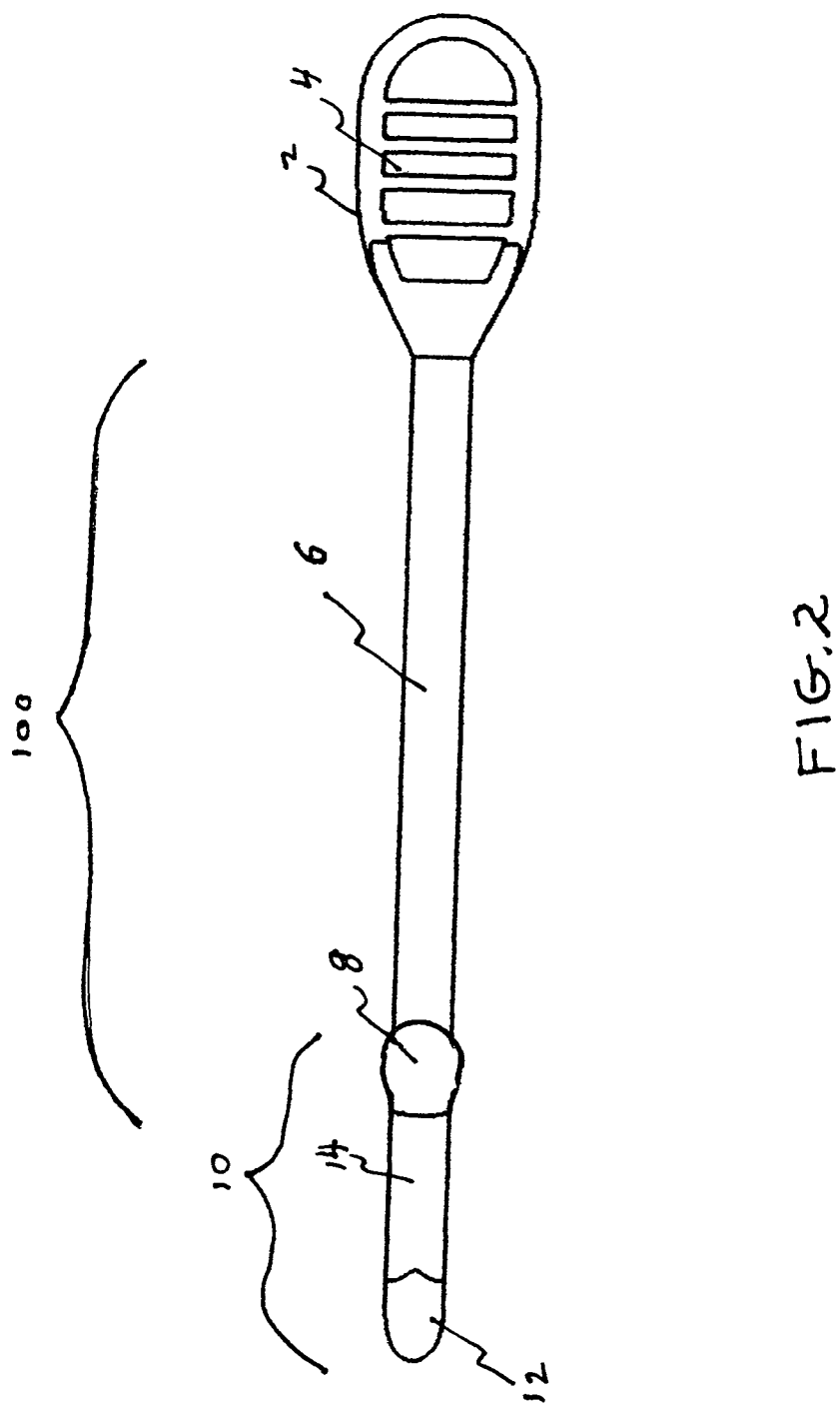
FIG. 2 is a top plan view of the invention.

FIG. 2 is a top plan view of the invention 100. Elongate member 6 can be a circular cross section approximately one quarter of an inch in diameter, but can also be a square or elliptical cross section. Flat plate 2 is oval in shape and the width of the plate is approximately one half of an inch which helps the user have greater control over the removal tool 100 during use.

Figure 3:
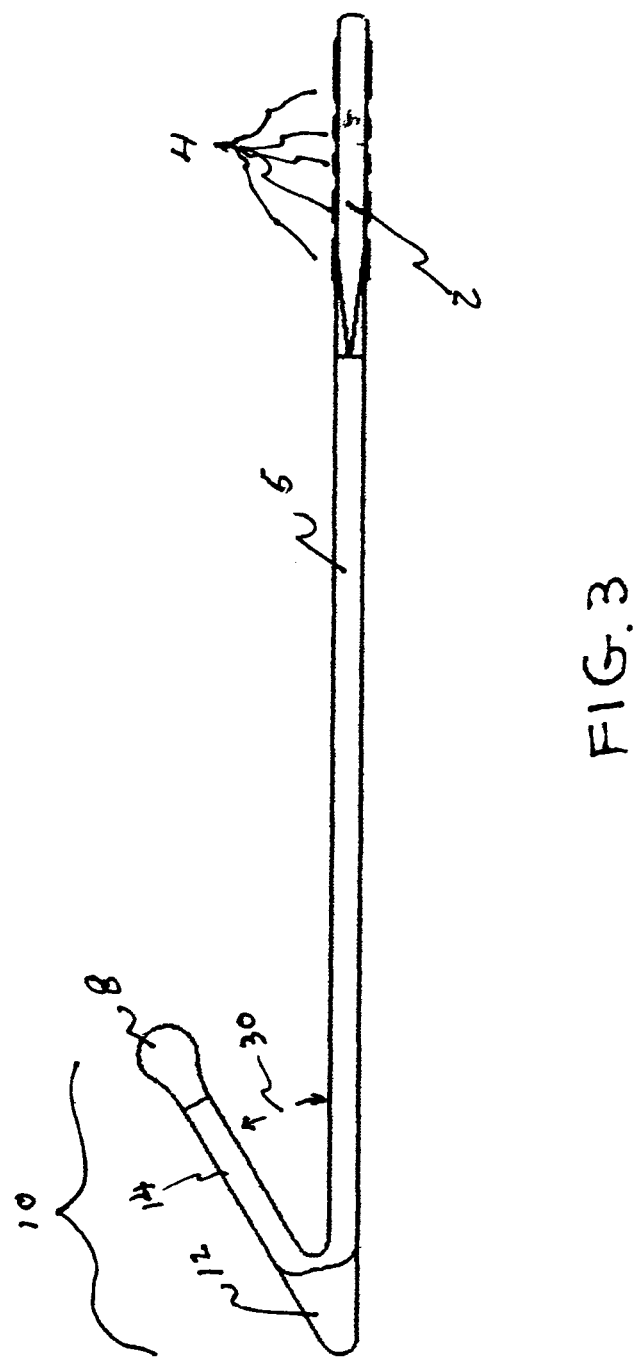
FIG. 3 is a side view of the invention.

FIG. 3 is a side view of the invention 100. Gripping strips 4 can be seen as raised approximately seventy thousandths of an inch from the top and bottom surface of plate 2. These raised strips 4 are molded from a resilient thermoplastic elastomer that has a high stiction factor, to further facilitate the user's control of the removal tool 100 during use. The angle of the hook portion 10 is approximately forty degrees as shown by dimension line 30.

Figure 4:
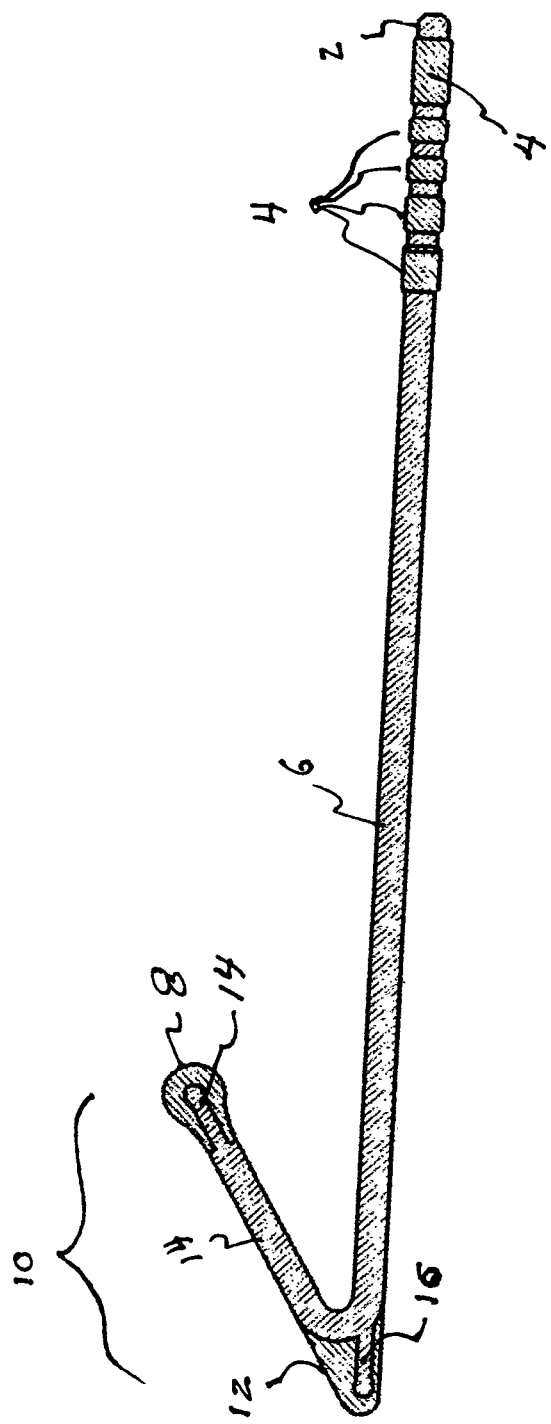
FIG. 4 is a side section view of the invention.

FIG. 4 is a side section view longitudinally bisecting the invention 100. Extension posts 14, 16 help anchor the co-molded tips 12, 8 so that they will remain firmly attached to the hook let 14 and hook 10 front tip.

The above described and illustrated invention helps any woman who uses an estrogen ring or other medical ring type product to easily and safely remove the ring from the vaginal canal.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

The invention claimed is:

1. A drug dispensing ring removal tool comprising: a rigid elongate member;
   a rigid hook member fixedly attached to a proximal end of the elongate member, the hook member comprising a tip and a forward most end;
   a rigid flat plate member fixedly attached to a distal end of the elongate member, the rigid flat plate member comprising cutout portions and a planar surface;
   a hook tip resilient member fixedly attached to the tip of the hook member;
   a hook front end resilient member fixedly attached to the forward most end of the hook member; and
   a plurality of flat plate resilient members fixedly attached within cutout portion of the flat plate member, the flat plate resilient members extending approximately one sixteenth of an inch above the planar surface of the plate member.

2. The drug dispensing ring removal tool as claimed in claim 1 wherein a length from a distal end of the flat plate member to the proximal end of the elongate member is approximately six inches.

3. The drug dispensing ring removal tool as claimed in claim 1 wherein said hook member is offset from said elongate member by approximately forty degrees.

4. The drug dispensing ring removal tool as claimed in claim 1 wherein a length from a free end of the hook tip resilient member to the forward most end of the hook member is approximately one and one quarter inches.

5. The drug dispensing ring removal tool as claimed in claim 1 wherein said elongate member and said hook member each have a cross section diameter of approximately one quarter of an inch.

6. The drug dispensing ring removal tool as claimed in claim 1 wherein said elongate member and said hook member are made of hypo-allergenic plastic.

7. The drug dispensing ring removal tool as claimed in claim 1 wherein
   the hook tip resilient member, the hook front end resilient member and said plurality of flat plate resilient members are made of thermoplastic elastomer.

\* \* \* \* \*